US010342624B2

(12) United States Patent
Shibazaki et al.

(10) Patent No.: US 10,342,624 B2
(45) Date of Patent: Jul. 9, 2019

(54) MEDICAL MANIPULATOR SYSTEM

(71) Applicant: OLYMPUS CORPORATION, Tokyo (JP)

(72) Inventors: Takami Shibazaki, Kanagawa (JP); Kosuke Kishi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 205 days.

(21) Appl. No.: 15/657,252

(22) Filed: Jul. 24, 2017

(65) Prior Publication Data
US 2017/0319285 A1 Nov. 9, 2017

Related U.S. Application Data

(63) Continuation of application No. PCT/JP2016/064645, filed on May 17, 2016.

(30) Foreign Application Priority Data

May 21, 2015 (JP) .................................. 2015-103737

(51) Int. Cl.
*G06F 19/00* (2018.01)
*A61B 34/00* (2016.01)
(Continued)

(52) U.S. Cl.
CPC .............. *A61B 34/70* (2016.02); *A61B 34/30* (2016.02); *A61B 34/37* (2016.02); *A61B 34/71* (2016.02);
(Continued)

(58) Field of Classification Search
None
See application file for complete search history.

(56) References Cited

U.S. PATENT DOCUMENTS

2007/0027459 A1 2/2007 Horvath et al.
2007/0083480 A1 4/2007 Ozaki et al.
(Continued)

FOREIGN PATENT DOCUMENTS

EP 2064984 A2 6/2009
EP 2213221 A1 8/2010
(Continued)

OTHER PUBLICATIONS

Extended Supplementary European Search Report dated Jan. 17, 2019 in European Patent Application No. 16 79 6509.4.
(Continued)

*Primary Examiner* — Bhavesh V Amin
(74) *Attorney, Agent, or Firm* — Scully, Scott, Murphy & Presser, P.C.

(57) ABSTRACT

Provided is a medical manipulator system including: a manipulator including an end effector configured to treat a patient and a driver configured to drive the end effector; an operation input unit configured to generate an operation command for the manipulator; a storage configured to store a history information of each operator; and a controller comprising one or more processors, the one or more processors configured to: receive identification information of an operator by inputting of the operation input unit; get the history information of the operator from the storage based on the identification information; estimate a skill of the operator based on the history information; set a maximum operating speed of the manipulator and/or an operating range of the manipulator in proportion to the skill; qualify the operation command based on the maximum operating speed and/or the operating range; and control the driver based on the qualified operation command.

9 Claims, 14 Drawing Sheets

(51) Int. Cl.
    *A61B 34/37*         (2016.01)
    *B25J 9/16*          (2006.01)
    *A61B 34/30*         (2016.01)
    *G16H 40/67*        (2018.01)
    *G16H 20/40*        (2018.01)
    *A61B 17/00*        (2006.01)
    *A61B 90/90*        (2016.01)
    *A61B 90/00*        (2016.01)

(52) U.S. Cl.
    CPC ............... *A61B 34/74* (2016.02); *B25J 9/163* (2013.01); *B25J 9/1666* (2013.01); *G16H 20/40* (2018.01); *G16H 40/67* (2018.01); *A61B 90/90* (2016.02); *A61B 2017/00221* (2013.01); *A61B 2017/00225* (2013.01); *A61B 2017/00389* (2013.01); *A61B 2034/301* (2016.02); *A61B 2090/0803* (2016.02); *A61B 2090/0807* (2016.02)

(56) References Cited

U.S. PATENT DOCUMENTS

| | | |
|---|---|---|
| 2007/0156285 A1 | 7/2007 | Sillman et al. |
| 2009/0143642 A1 | 6/2009 | Takahashi et al. |
| 2011/0098861 A1 | 4/2011 | Sillman et al. |
| 2012/0189996 A1 | 7/2012 | Hager et al. |
| 2012/0330613 A1 | 12/2012 | Sillman et al. |
| 2014/0135984 A1 | 5/2014 | Hirata |
| 2014/0304638 A1 | 10/2014 | Yoshikawa et al. |
| 2016/0098933 A1 | 4/2016 | Reiley et al. |

FOREIGN PATENT DOCUMENTS

| | | |
|---|---|---|
| EP | 2 730 377 A2 | 5/2014 |
| EP | 2772219 A1 | 9/2014 |
| JP | 2002-085333 A | 3/2002 |
| JP | 2002-154085 A | 5/2002 |
| JP | 2004-129782 A | 4/2004 |
| JP | 2008-221363 A | 9/2008 |
| JP | 2009-502337 A | 1/2009 |
| JP | 4580973 B2 | 11/2010 |
| JP | 2012-014407 A | 1/2012 |
| JP | 2012-521568 A | 9/2012 |
| JP | 2013-090722 A | 5/2013 |
| JP | 2014-094436 A | 5/2014 |
| WO | WO 2007/016101 A1 | 2/2007 |
| WO | 2007/114868 A2 | 10/2007 |
| WO | WO 2010/108128 A2 | 9/2010 |

OTHER PUBLICATIONS

International Search Report dated Aug. 16, 2016 issued in PCT/JP2016/064645.

US 10,342,624 B2

MEDICAL MANIPULATOR SYSTEM

CROSS-REFERENCE TO RELATED APPLICATIONS

This is a continuation of International Application PCT/JP2016/064645, with an international filing date of May 17, 2016, which is hereby incorporated by reference herein in its entirety. This application claims the benefit of Japanese Patent Application No. 2015-103737, the content of which is incorporated herein by reference.

TECHNICAL FIELD

The present invention relates to medical manipulator systems.

BACKGROUND ART

A known system in the related art collects data related to a surgical operation performed by an operator using a surgical device and quantifies the clinical skill of the operator based on the collected surgical-operation-related data (for example, see Patent Literature 1).

CITATION LIST

Patent Literature

PTL 1

The Publication of Japanese Patent No. 4580973

SUMMARY OF INVENTION

An aspect of the present invention provides a medical manipulator system including: a manipulator including an end effector configured to treat a patient and a driver configured to drive the end effector; an operation input unit configured to generate an operation command for the manipulator; a storage configured to store a history information of each operator; and a controller comprising one or more processors, the one or more processors configured to: receive identification information of an operator by inputting of the operation input unit; get the history information of the operator from the storage based on the identification information; estimate a skill of the operator based on the history information; set a maximum operating speed of the manipulator and/or an operating range of the manipulator in proportion to the skill; qualify the operation command based on the maximum operating speed and/or the operating range; and control the driver based on the qualified operation command.

Another aspect of the present invention provides a medical manipulator system including: a manipulator including an end effector configured to treat a patient and a driver configured to drive the end effector; an operation input unit configured to generate an operation command for the manipulator; and a first storage configured to store a history information of each operator; a second storage configured to store medical information; a display configured to display a state of the manipulator; and a controller comprising one or more processors, the one or more processors configured to: receive identification information of an operator by inputting of the operation input unit; get the history information of the operator from the first storage based on the identification information; estimate a skill of the operator based on the history information; get the medical information from the second storage based on the estimated skill; and control the display so as to display the medical information.

DESCRIPTION OF EMBODIMENTS

A medical manipulator system 1 according to a first embodiment of the present invention will be described below with reference to the drawings.

Figure 1:
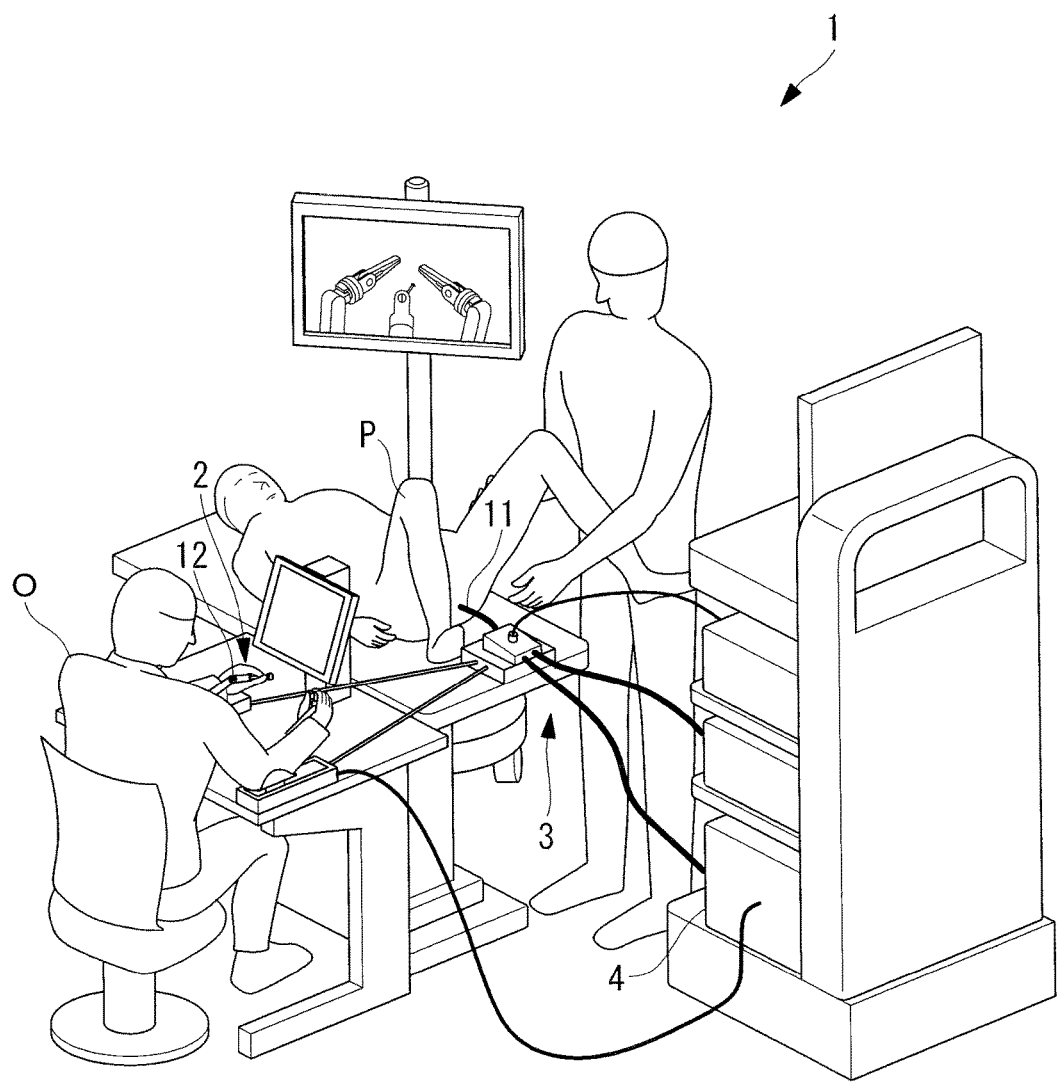
FIG. 1 illustrates the overall configuration of a medical manipulator system according to a first embodiment of the present invention.
Figure 2:
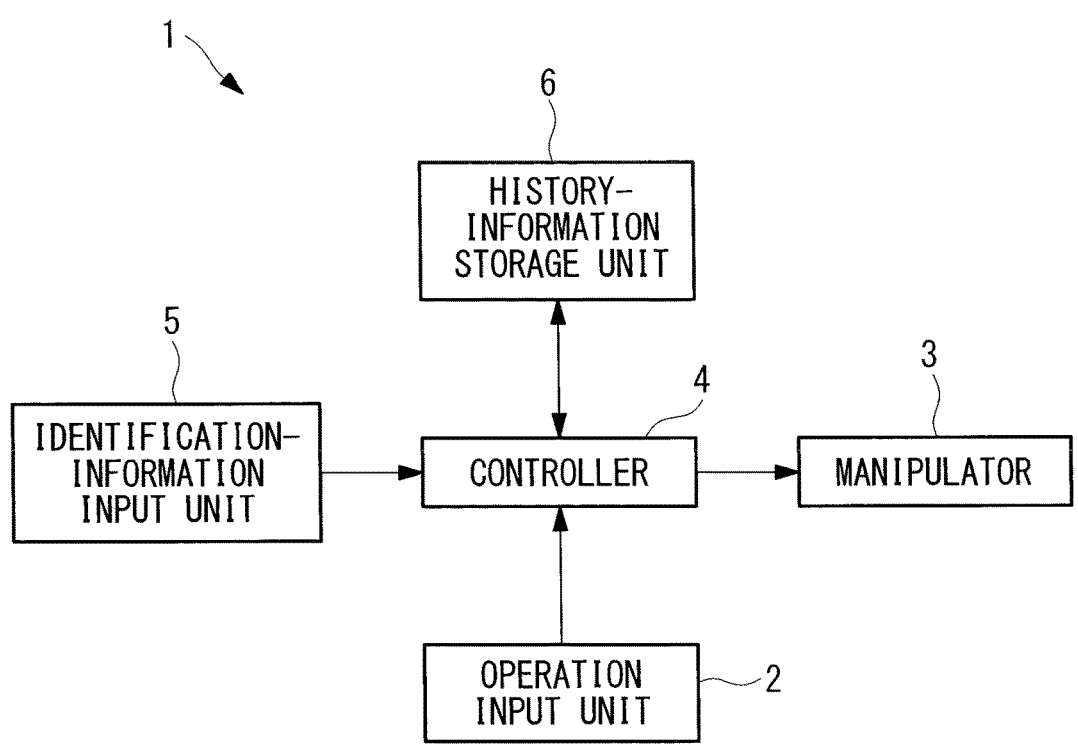
FIG. 2 is a block diagram illustrating the medical manipulator system in FIG. 1.
Figure 3:
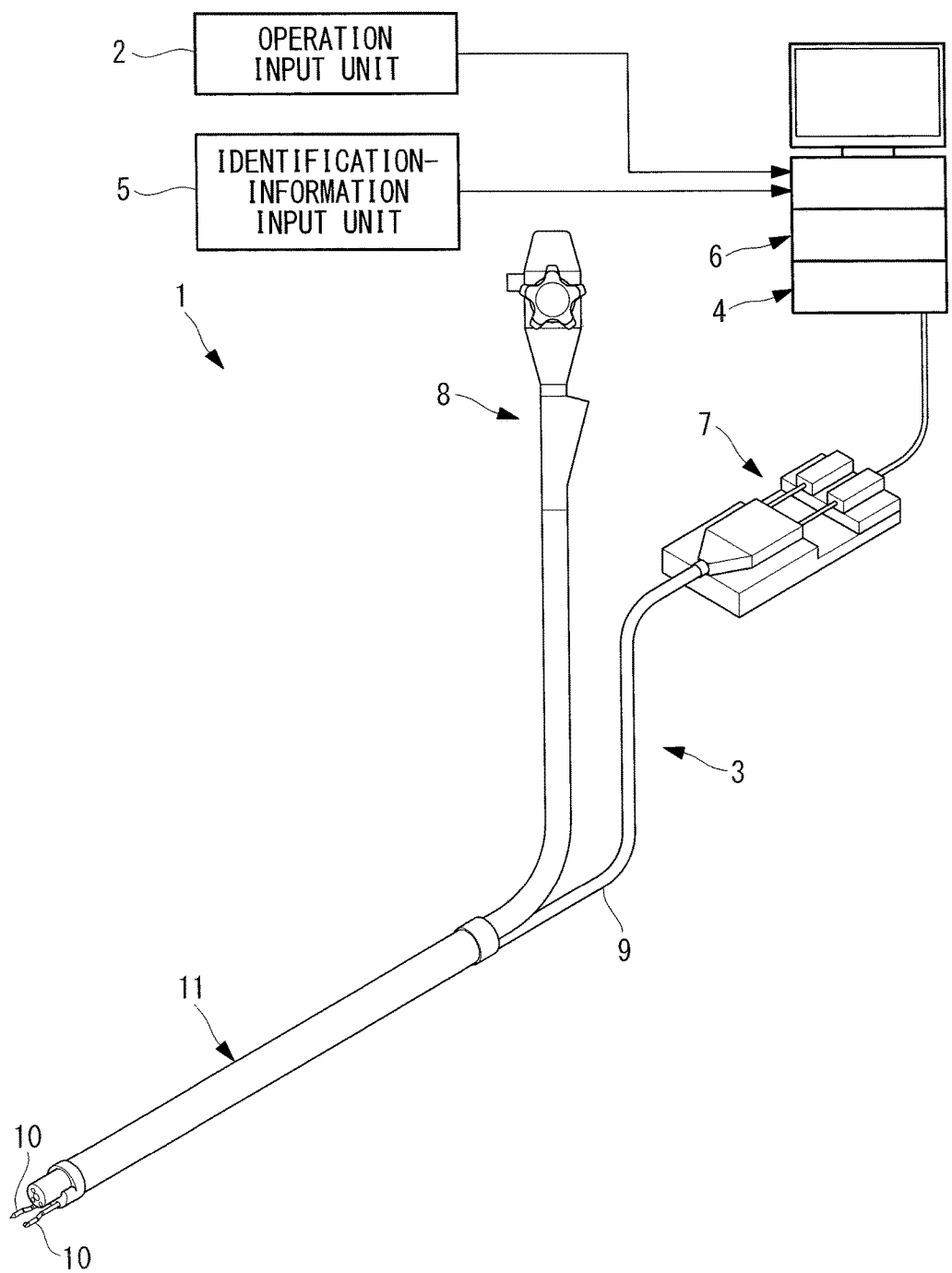
FIG. 3 is a perspective view illustrating a manipulator included in the medical manipulator system in FIG. 1.

As shown in FIGS. 1 to 3, the medical manipulator system 1 according to this embodiment includes an operation input unit 2 to be operated by an operator O, a manipulator 3 to be inserted into the body cavity of a patient P, a controller 4 that controls a driver 7 based on an operation command input via the operation input unit 2, an identification-information input unit 5 used for inputting identification information of the operator O, and a history-information storage unit 6 that stores history information of operations performed on the operation input unit 2 by the operator O.

As shown in FIG. 3, the manipulator 3 includes an insertion section 9 that is to be inserted into the body cavity of the patient P directly or via, for example, an overtube 11 or a channel of a flexible endoscope 8 to be inserted into the body cavity of the patient P, two surgical instruments (surgical sections) 10 disposed at the distal end of the insertion section 9, and the driver 7 that is disposed at the base end of the insertion section 9 and that drives the surgical instruments 10.

FIG. 3 illustrates a case where the overtube 11 used has two channels through which the endoscope 8 and the insertion section 9 of the manipulator 3 extend.

Each surgical instrument 10 has one or more joints and is used for medically treating an affected area inside the body of the patient P. The surgical instruments 10 include, for example, forceps, injection needles, or cauterizing electrodes and are selected, as appropriate, in accordance with the type of treatment. The number of surgical instruments 10 is not limited to two, and may alternatively be one or three or more.

Power generated by the driver 7 is transmitted to the surgical instruments 10 via, for example, wires (not shown) or power transmission members, such as cables, so that the surgical instruments 10 can be driven.

The operation input unit 2 is used for inputting an operation command for operating the surgical instruments 10 and has a freely-chosen operable section, such as a lever 12, a switch, a push button, or a slide switch. For example, in the case of an operable section with a continuously-changeable tilt angle, like the lever 12, an operation command for continuously operating the surgical instruments 10 can be input by continuously changing the tilt angle of the lever 12.

The identification-information input unit 5 is a freely-chosen input device, such as a keyboard, a mouse, or a bar-code reader, and can be used for inputting identification information of the operator O.

The controller 4 generates a command signal for actuating the driver 7 based on the operation command input via the operation input unit 2.

Furthermore, the medical manipulator system 1 according to this embodiment includes the history-information storage unit 6 that stores history information of operations performed on the operation input unit 2 by the operator O in association with the identification information of the operator O.

Figure 4:
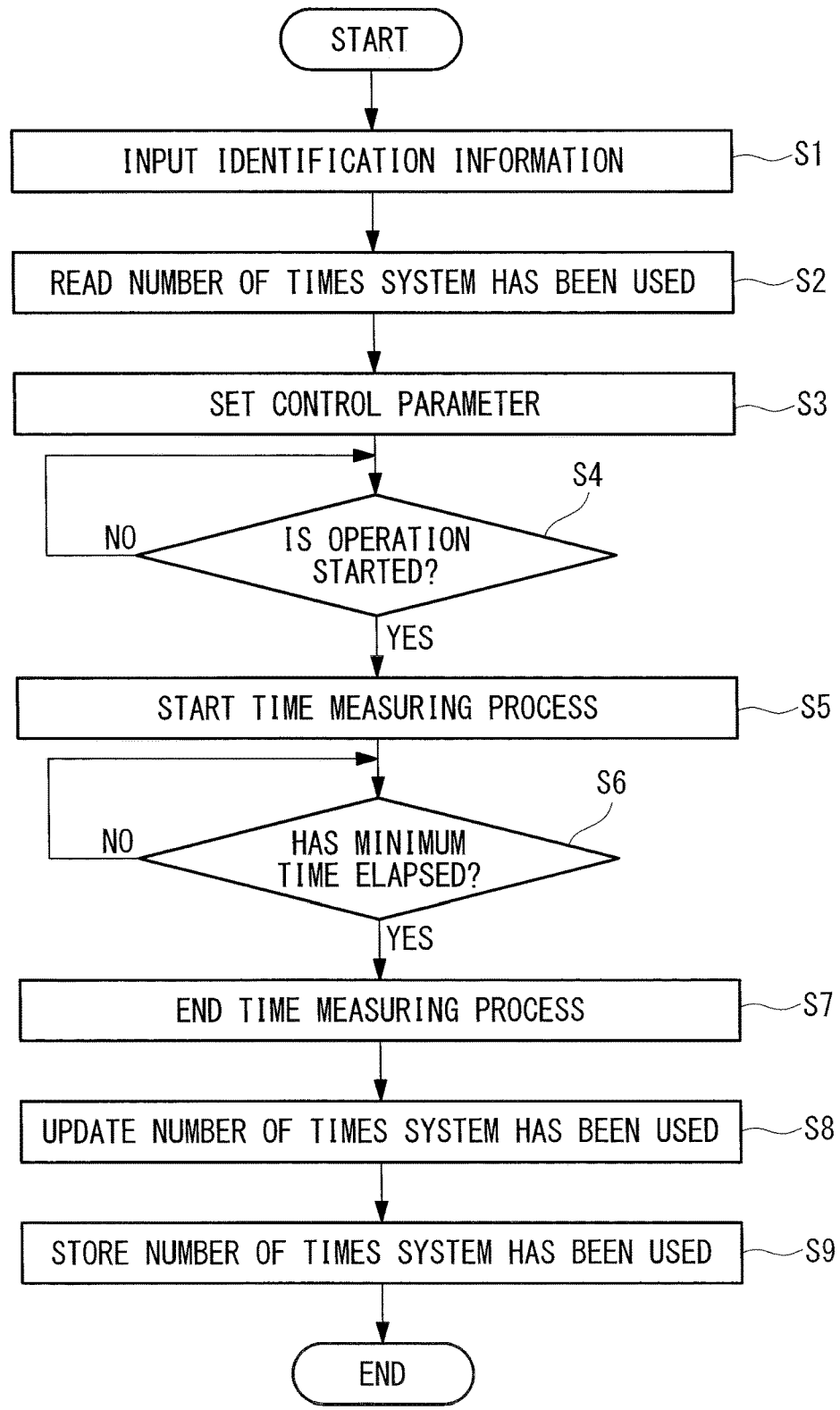
FIG. 4 is a flowchart explaining processing of operational history information in the medical manipulator system in FIG. 1.

An example of the history information of operations includes the number of times the medical manipulator system 1 is used by the operator O. For example, as shown in FIG. 4, when the power of the medical manipulator system 1 is turned on and the operator O inputs identification information via the identification-information input unit 5 (step S1), the controller 4 reads the number of times the system has been used as history information from the history-information storage unit 6 (step S2). Then, when an operation is started on the operation input unit 2 (step S4), the controller 4 causes a timer to start measuring the time (step S5). If the operation input unit 2 is operated beyond a minimum period of time required for the treatment (step S6), the controller 4 ends the time measuring process (step S7), updates the number of times the system has been used by adding a value of 1 thereto (step S8), and stores the updated number of times the system has been used in the history-information storage unit 6 (step S9).

Then, in the medical manipulator system 1 according to this embodiment, the controller 4 sets a control parameter based on the number of times the system has been used by the operator O read from the history-information storage unit 6 (step S3). Examples of the control parameter include the maximum operating speed and/or the operating range of the driver 7.

As the number of times the medical manipulator system 1 is used, which is the history information of the operator O, becomes larger, the controller 4 estimates that the operator O has a high operational skill and increases the maximum operating speed of the driver 7 and/or expands the operating range of the driver 7.

The operation of the medical manipulator system 1 according to this embodiment having the above-described configuration will be described below.

In order to medically treat an affected area located inside the body cavity of the patient P by using the medical manipulator system 1 according to this embodiment, the operator O first turns on the power of the medical manipulator system 1 and inputs his/her identification information via the identification-information input unit 5.

When the identification information is input, the controller 4 searches through the history-information storage unit 6 by using the input identification information as a key and reads history information stored in association with the identification information. Then, the controller 4 sets the control parameter based on the history information.

In a state where the operator O has inserted the insertion section 9 of the manipulator 3 into the body and has caused the surgical instruments 10 disposed at the distal end of the insertion section 9 to face the affected area, the operator O operates the operation input unit 2 so as to input an operation command. Thus, the controller 4 generates a control signal for controlling the driver 7 in accordance with the input operation command and outputs the control signal to the driver 7.

In this case, the controller 4 generates the control signal by using the control parameter set based on the number of times the system has been used read from the history-information storage unit 6. Specifically, from the history information stored in the history-information storage unit 6, it is determined whether or not the number of times the medical manipulator system 1 is used by the operator O is larger than a predetermined number of times the system has been used. If larger than the predetermined number of times the system has been used, it is estimated that the operator O is highly skilled, and a control signal is generated such that the maximum operating speed is increased and/or the operating range of the driver 7, that is, the operating range of the surgical instruments 10, is expanded. The predetermined number of times the system has been used for estimating the skill of the operator O may be provided in a plurality of levels or may be associated with the number of times the system has been used.

If the operator O is highly skilled, proper treatment can be performed even by quickly moving the surgical instruments 10. By quickly moving the surgical instruments 10, the treatment efficiency can be improved. Moreover, if the operator O is highly skilled, the operating range may be expanded so as to enable free movement with few limitations, which is advantageous in terms of improved ease of treatment with fewer limitations and improved treatment efficiency.

In contrast, if the skill of the operator O is low, wasteful movement caused by the manipulator 3 moving unintentionally at high speed can be avoided by limiting the maximum operating speed, thereby enabling improved treatment efficiency. Moreover, if the skill of the operator O is low, the operating range may be reduced so as to avoid contact with surrounding tissue, which may be caused when the manipulator 3 moves to an unintended range, thereby advantageously enabling improved treatment efficiency.

Accordingly, in the medical manipulator system 1 according to this embodiment, the controller 4 sets the control parameter so as to increase the maximum operating speed of the driver 7 and/or expand the operating range of the driver 7 as the operational skill of the operator O estimated based on the history information of operations stored in the history-information storage unit 6 becomes higher. This enables improved treatment efficiency regardless of the skill of the operator O.

Furthermore, the control parameter may be set in accordance with the skill of the operator O and the type of surgical instruments 10 to be used. Accordingly, this enables proper control for each surgical instrument 10 to be used, thereby enabling improved treatment efficiency.

Next, a medical manipulator system 13 according to a second embodiment of the present invention will be described below with reference to the drawings.

In the description of this embodiment, components identical to those in the medical manipulator system 1 according to the first embodiment described above will be given the same reference signs, and descriptions thereof will be omitted.

Figure 5:
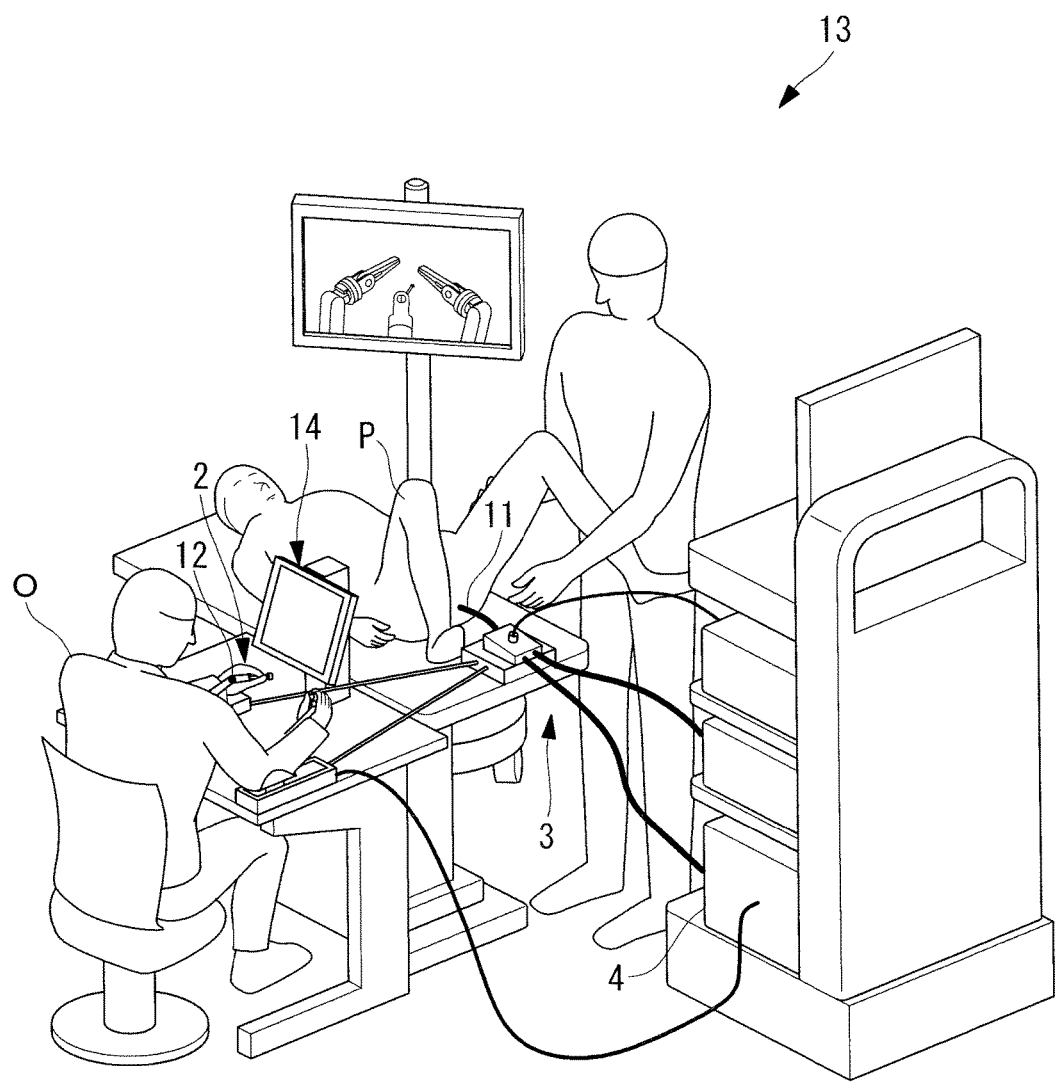
FIG. 5 illustrates the overall configuration of a medical manipulator system according to a second embodiment of the present invention.
Figure 6:
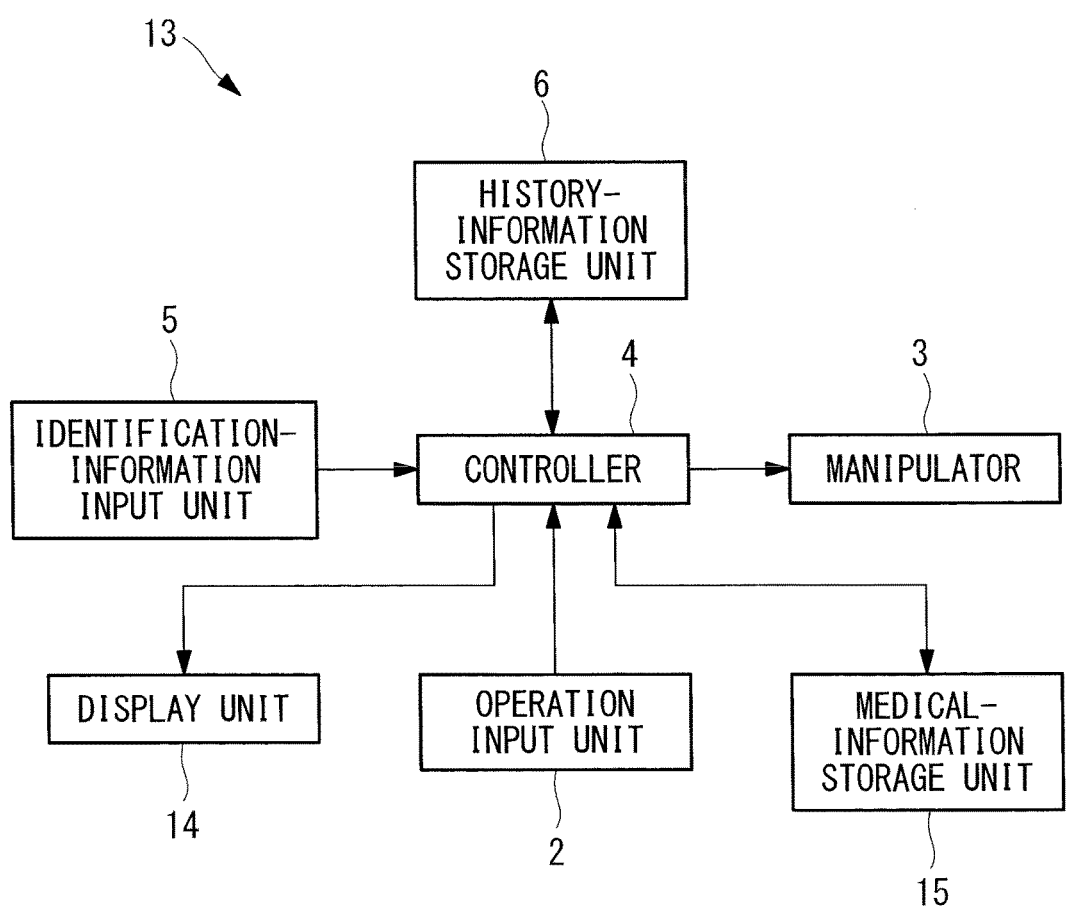
FIG. 6 is a block diagram illustrating the medical manipulator system in FIG. 5.
Figure 7:
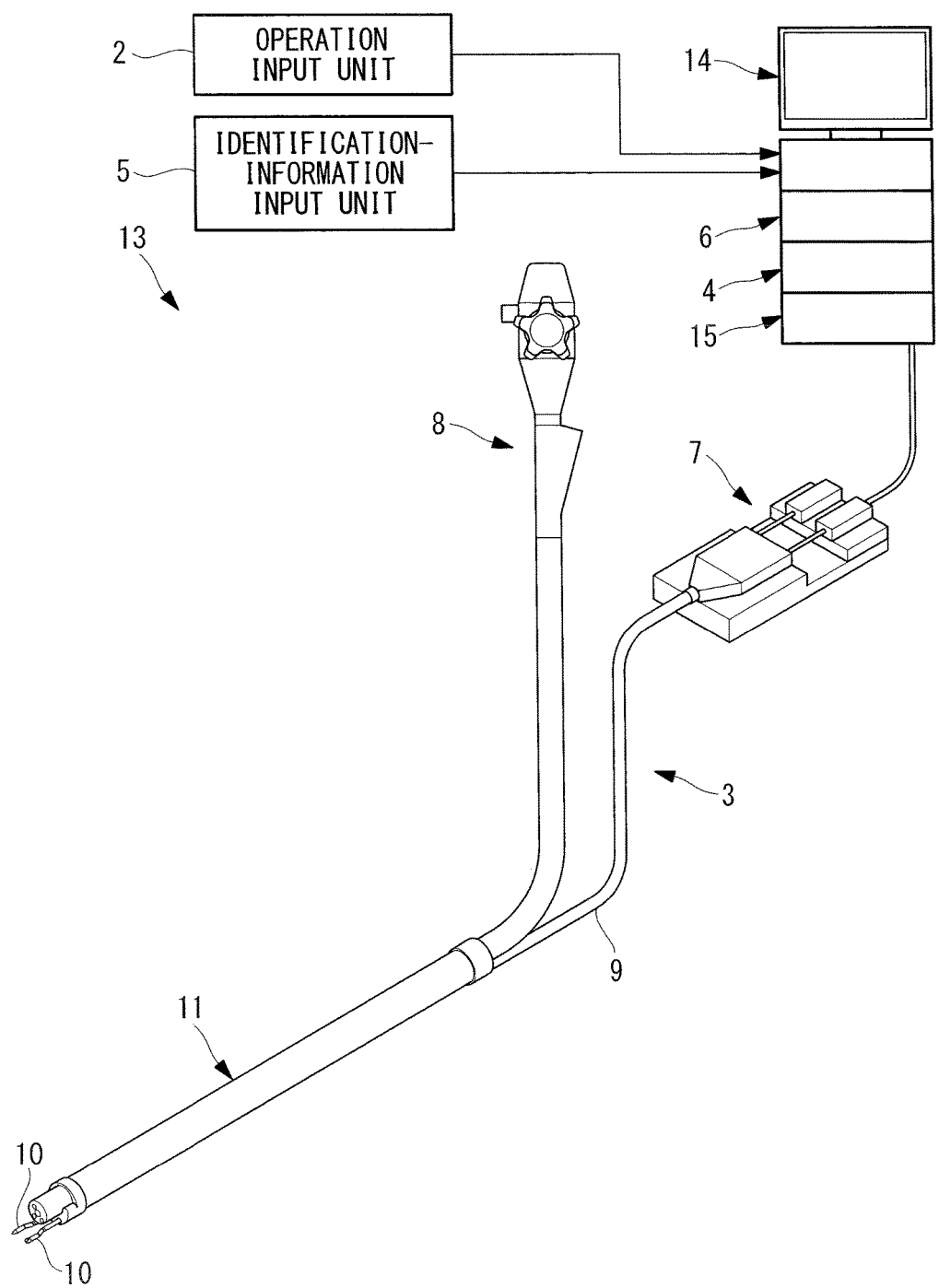
FIG. 7 is a perspective view illustrating a manipulator included in the medical manipulator system in FIG. 5.

As shown in FIGS. 5 to 7, the medical manipulator system 13 according to this embodiment differs from the medical manipulator system 1 according to the first embodiment in that it includes a display unit 14 that displays the operational state of the manipulator 3 and a medical-information storage unit 15 that stores medical information associated with the skill of the operator O.

The medical-information storage unit 15 stores, as the medical information, medical-device information set for each skill level of the operator O.

Figure 8:
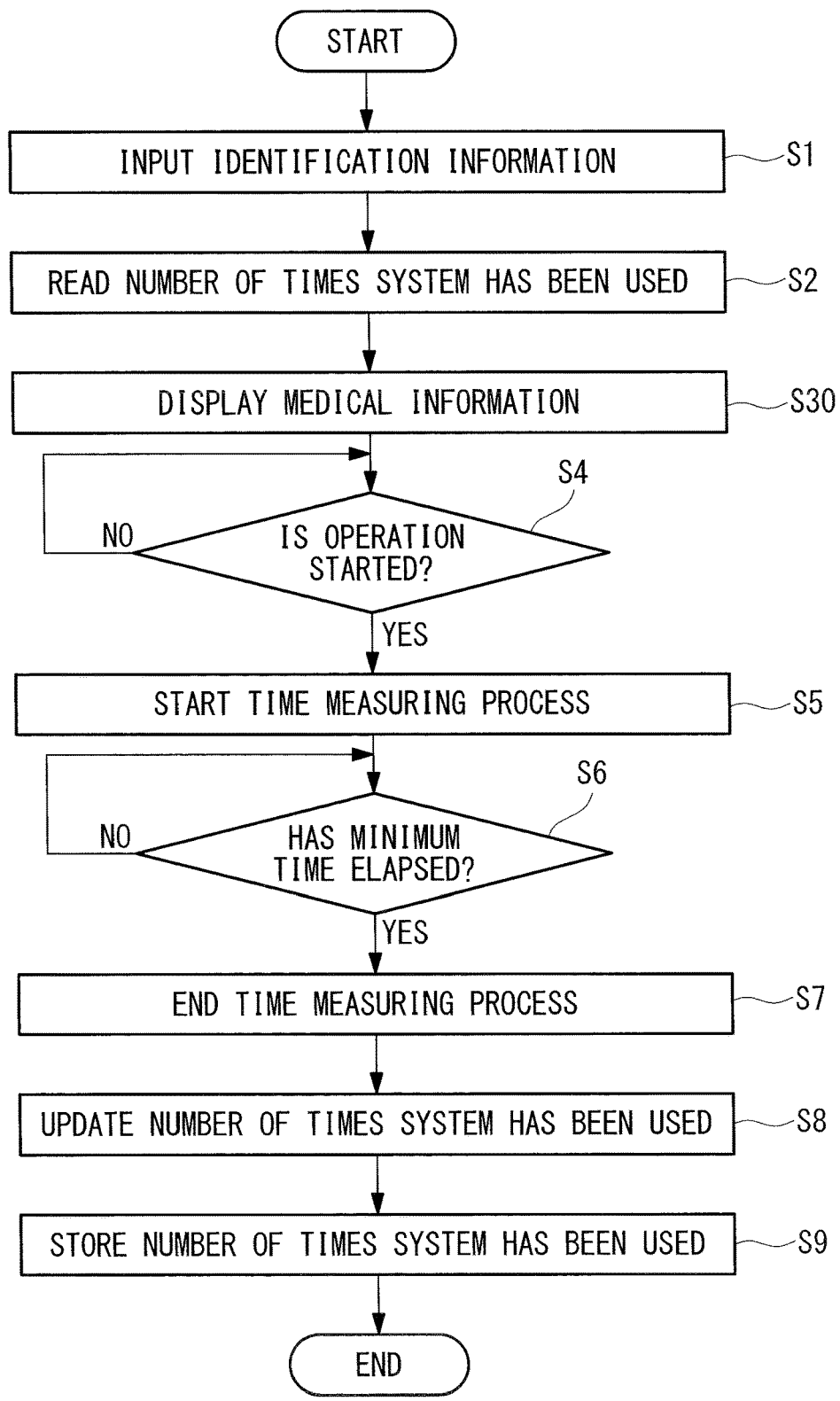
FIG. 8 is a flowchart explaining processing of operational history information in the medical manipulator system in FIG. 5.

An example of the history information of operations includes the number of times the medical manipulator system 13 is used by the operator O. For example, as shown in FIG. 8, when the power of the medical manipulator system 13 is turned on and identification information is input via the identification-information input unit 5 (step S1), the controller 4 reads the number of times the system has been used as history information from the history-information storage unit 6 (step S2). Then, when an operation is started on the operation input unit 2 (step S4), the controller 4 causes a timer to start measuring the time (step S5). If the operation input unit 2 is operated beyond a minimum period of time required for the treatment (step S6), the controller 4 ends the time measuring process (step S7), updates the number of times the system has been used by adding a value of 1 thereto (step S8), and stores the updated number of times the system has been used in the history-information storage unit 6 (step S9).

Then, as shown in FIG. 8, in the medical manipulator system 13 according to this embodiment, the controller 4 causes the display unit 14 to display the medical-device information based on the number of times the system has been used by the operator O read from the history-information storage unit 6 (step S30).

As the number of times the medical manipulator system 13 is used, which is the history information of the operator O, becomes larger, the controller 4 estimates that the operator O has a high operational skill, reads the medical-device information associated with the operational skill from the medical-information storage unit 15, and causes the display unit 14 to display the medical-device information.

In this case, when the identification information is input, the controller 4 searches through the history-information storage unit 6 by using the input identification information as a key and reads history information stored in association with the identification information. Then, the controller 4 quantifies the skill of the operator O based on the history information and causes the display unit 14 to display the medical-device information.

Based on the displayed medical-device information, the operator O installs an appropriate medical device according to his/her skill.

Accordingly, in a case where the operator O is highly skilled, information related to a medical device that requires a high skill but enables high treatment efficiency is displayed on the display unit 14, so as to prompt the operator O to install the medical device that enables high treatment efficiency. As a result, the operator O performs the treatment using a medical device suitable for his/her high skill, thereby enabling improved treatment efficiency.

If the skill of the operator O is low, information related to a medical device that does not require a high skill, that is, a medical device that can be operated relatively easily, is displayed on the display unit 14, so as to prompt the operator O to install the medical device that can be operated relatively easily. As a result, the operator O uses a medical device suitable for his/her skill, thereby enabling improved treatment efficiency.

Although medical-device information is stored as the medical information in the medical-information storage unit 15 in this embodiment, the medical information stored in the medical-information storage unit 15 may alternatively be learning-opportunity information in place of or in addition to the medical-device information.

Accordingly, learning opportunity information, such as seminar information, may be displayed on the display unit 14, so as to provide an appropriate opportunity for skill improvement to the operator O.

Moreover, a training program may be stored as the medical information in the medical-information storage unit 15. The operator O may perform training for a medical device suitable for his/her skill, so that the operator O can efficiently improve his/her skill.

Figure 9:
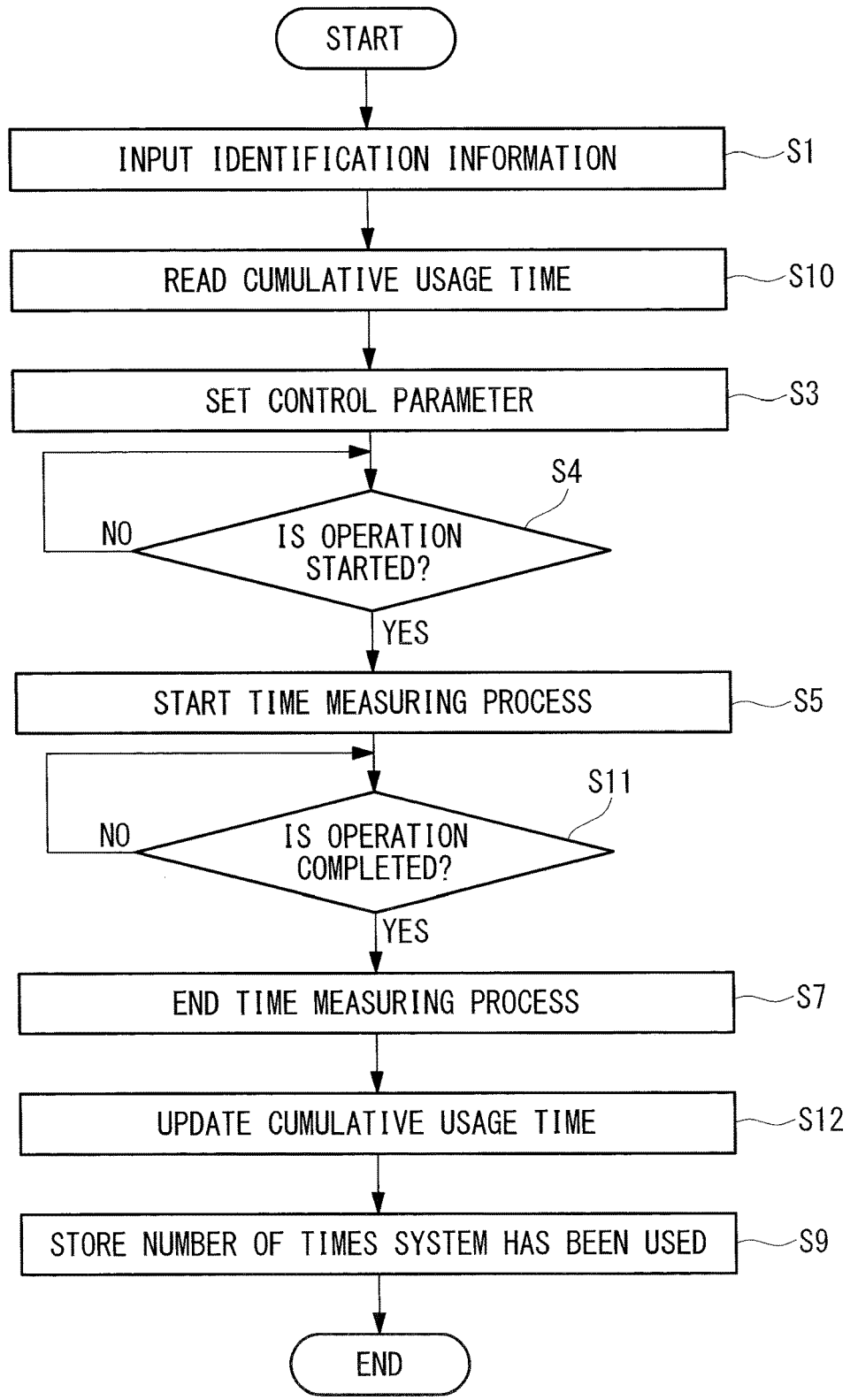
FIG. 9 is a flowchart explaining processing of operational history information in accordance with a modification of FIG. 4.
Figure 10:
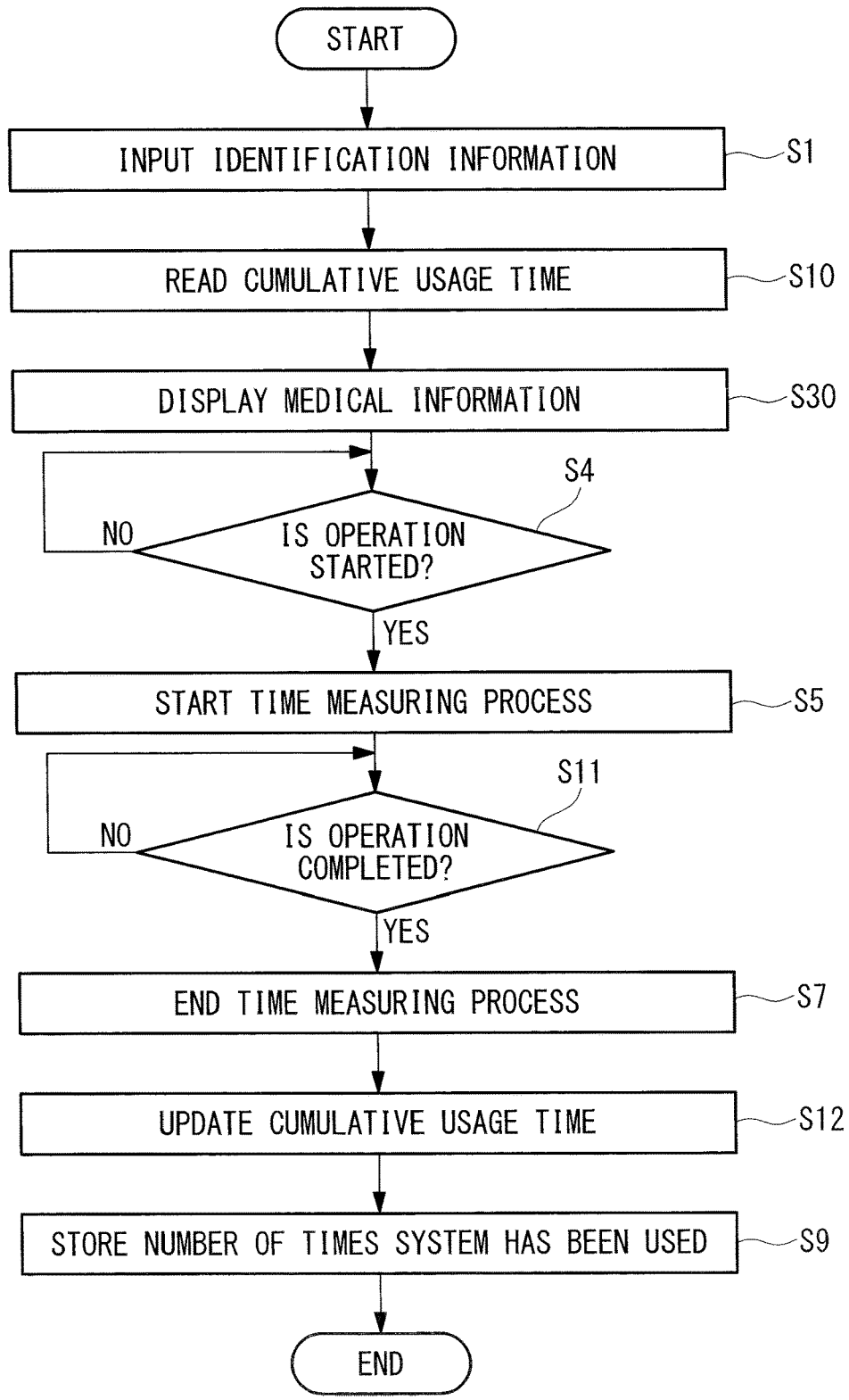
FIG. 10 is a flowchart explaining processing of operational history information in accordance with a modification of FIG. 8.

In the first and second embodiments described above, the number of times the medical manipulator system 1 or 13 is used by the operator O is used as the history information for estimating the operational skill of the operator O. Alternatively, as shown in FIGS. 9 and 10, a cumulative usage time of the medical manipulator system 1 or 13 may be used (step S10). In this case, the medical manipulator system 1 or 13 has a timer and causes the timer to start performing a time measuring process when an operation is started on the operation input unit 2. When the operation on the operation input unit 2 is completed (step S11), the controller 4 may cause the timer to end the time measuring process, update the cumulative usage time by adding the current usage time to the cumulative usage time already stored in the history-information storage unit 6 (step S12), and store the cumulative usage time.

The cumulative usage time is similar to the number of times the system has been used in that the operator O can be estimated to be highly skilled as the cumulative usage time becomes longer.

Figure 11:
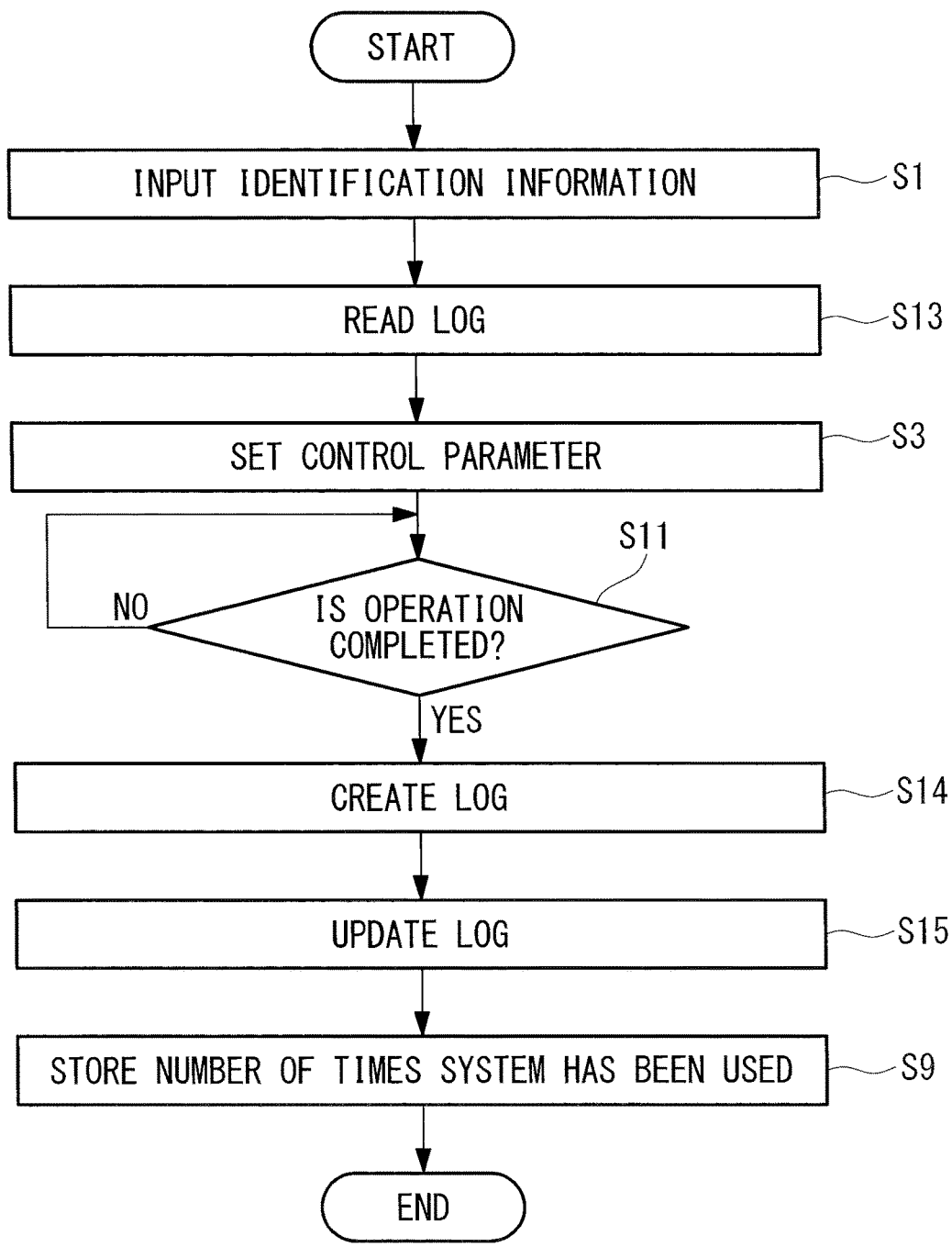
FIG. 11 is a flowchart explaining processing of operational history information in accordance with another modification of FIG. 4.
Figure 12:
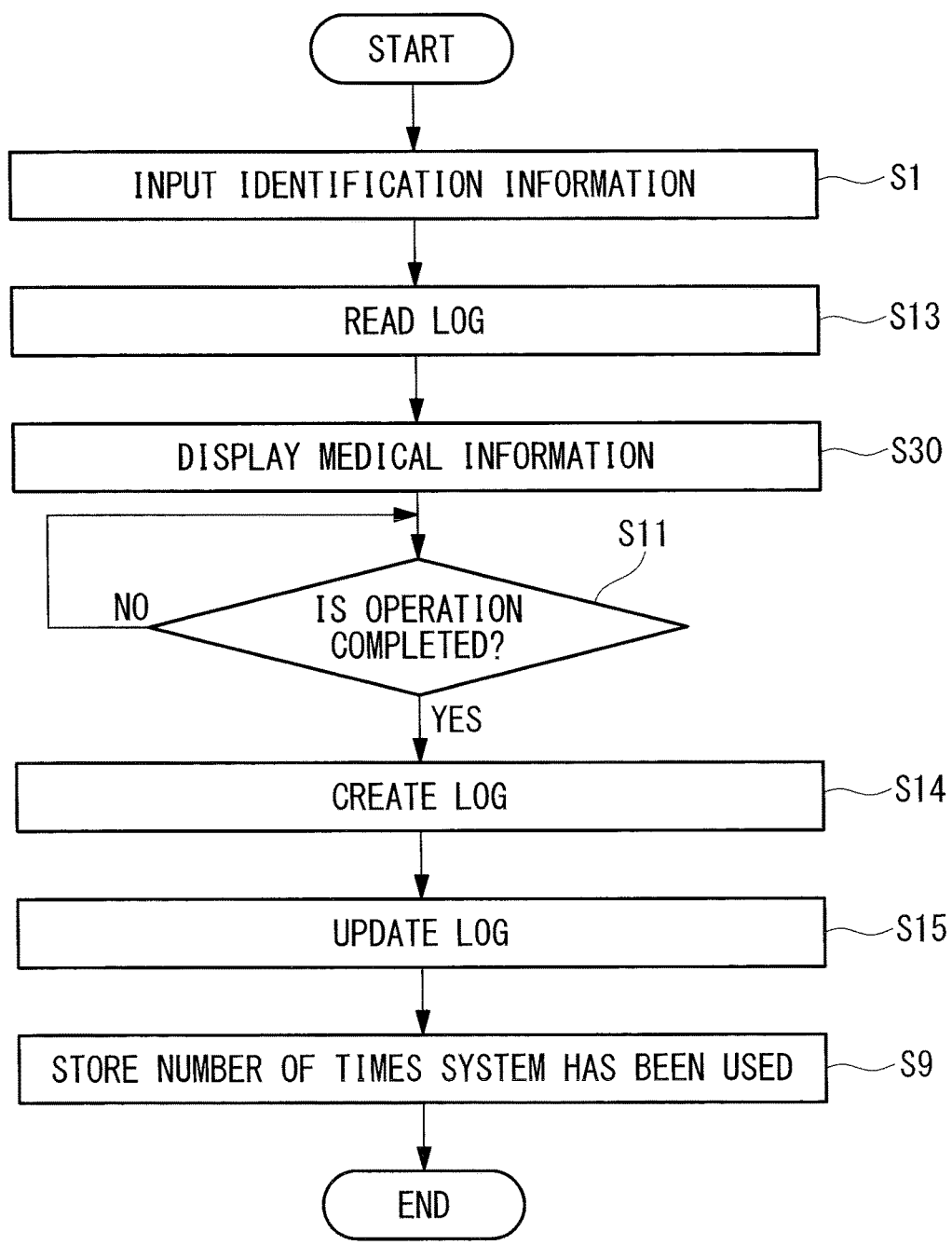
FIG. 12 is a flowchart explaining processing of operational history information in accordance with another modification of FIG. 8.

As the history information used for estimating the operational skill of the operator O, a non-usage (blank) period in which the medical manipulator system 1 or 13 is not used by the operator O may be employed. In this case, as shown in FIGS. 11 and 12, a log indicating the usage time and date of the medical manipulator system 1 or 13 may be stored in the history-information storage unit 6. When identification information of the operator O is input, the stored log may be read (step S13), and the non-usage period may be calculated by using the last usage time and date indicated in the read log. It can be estimated that the operational skill has deteriorated as the non-usage period becomes longer.

When the operation is completed, a new log may be created (step S14), and the log stored in the history-information storage unit 6 may be updated (step S15).

As the history information used for estimating the operational skill of the operator O, the time required for each treatment may be employed. In this case, the type of treatment may be inputtable, and the time required for each treatment may be measured and may be stored in association with the identification information of the operator O and the type of treatment.

Figure 13:
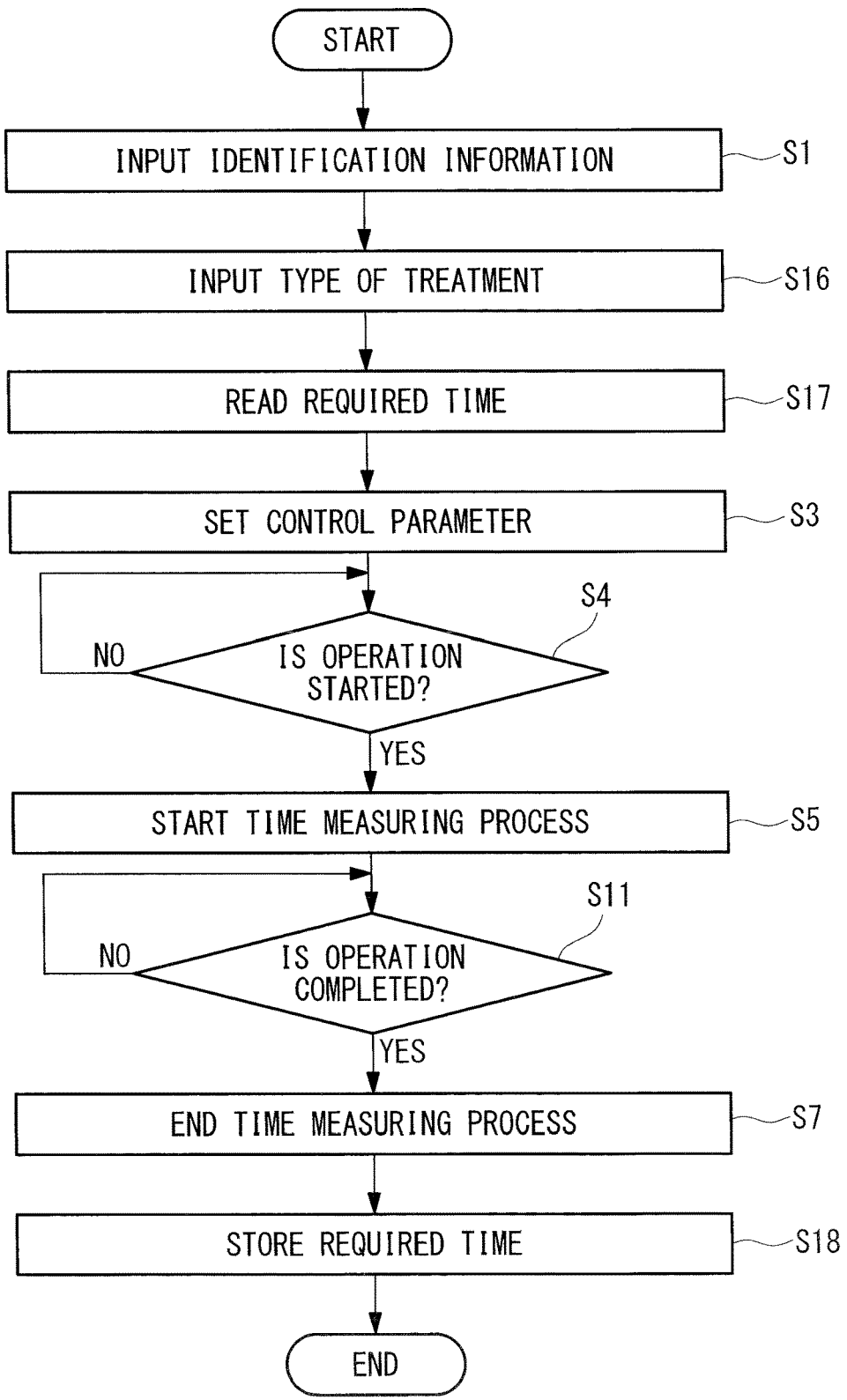
FIG. 13 is a flowchart explaining processing of operational history information in accordance with another modification of FIG. 4.
Figure 14:
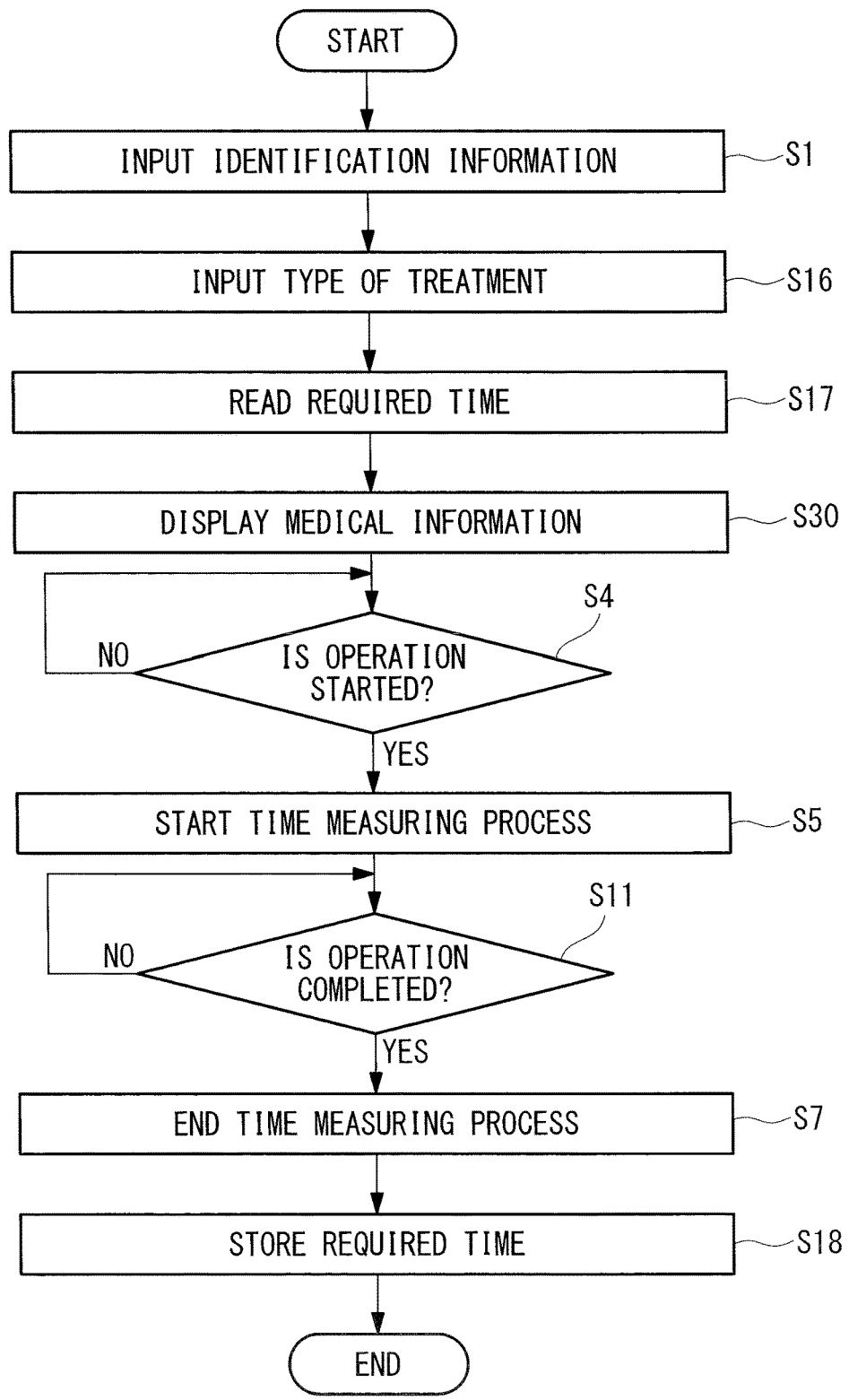
FIG. 14 is a flowchart explaining processing of operational history information in accordance with another modification of FIG. 8.

As shown in FIGS. 13 and 14, when actuating the medical manipulator system 1 or 13, the type of treatment is input (step S16) after the identification information is input. Then, the required time stored in the history-information storage unit 6 in association with the identification information of the operator O and the type of treatment is read (step S17), and the controller 4 sets the control parameter.

For example, the controller 4 may calculate, for each type of treatment, an average value, a minimum value, and a maximum value of the usage time stored in the history-information storage unit 6, and may estimate the operational skill of the operator O by comparing them with a standard time required for each treatment. It can be estimated that the operational skill of the operator O becomes lower as the required time becomes longer, and the control parameter may be set in accordance with the operational skill.

The timer may start performing the time measuring process when the operation of the operation input unit 2 is started, and may end the time measuring process when the operation is completed. Then, the current required time may be stored in association with the identification information of the operator O and the type of treatment (step S18).

By determining the operational skill in accordance with the required time for each type of treatment, it can be estimated whether the operational skill is high or low for each treatment with respect to a plurality of types of treatment performed by the same operator O using the same medical manipulator system 1 or 13, which is advantageous in that the estimation can be performed with high accuracy.

With regard to the standard required time for each treatment, the standard required time may be stored in the controller 4, or information stored in an external database may be acquired via a network.

Likewise, with regard to the medical-information storage unit 15, information stored in an external database may be acquired via a network. Consequently, latest medical information can be acquired from the external database so that an up-to-date status can be readily maintained.

In the first and second embodiments described above, the displaying of the medical information and the setting of the control parameter according to the skill of the operator O are described as individual embodiments. Alternatively, the displaying of the medical information and the setting of the control parameter may be combined.

Accordingly, by setting the control parameter, the efficiency of treatment to be executed can be improved, and information for making future treatment more efficient can be presented, thereby enabling improved treatment efficiency within a short period of time.

As a result, the above-described embodiments lead to the following aspects.

An aspect of the present invention provides a medical manipulator system including: a manipulator including an end effector configured to treat a patient and a driver configured to drive the end effector; an operation input unit configured to generate an operation command for the manipulator; a storage configured to store a history information of each operator; and a controller comprising one or more processors, the one or more processors configured to: receive identification information of an operator by inputting of the operation input unit; get the history information of the operator from the storage based on the identification information; estimate a skill of the operator based on the history information; set a maximum operating speed of the manipulator and/or an operating range of the manipulator in proportion to the skill; qualify the operation command based on the maximum operating speed and/or the operating range; and control the driver based on the qualified operation command.

According to this aspect, when the operator inputs the identification information via the identification-information input unit and operates the operation input unit, the controller controls the driver based on the operation command input via the operation input unit so as to actuate the surgical section of the manipulator, whereby medical treatment is performed on the patient. Then, the history information of the operation performed on the operation input unit by the operator during this treatment is stored in the history-information storage unit. When the operator performs subsequent treatment, the history information stored in the history-information storage unit in association with the identification information is read, and the maximum operating speed of the manipulator is increased and/or the operating range thereof is expanded as the skill of the operator estimated based on the history information becomes higher.

For a highly-skilled operator, high-speed treatment can be achieved by operating the manipulator at the maximum operating speed, thus enabling improved treatment efficiency. If the skill of the operator is low, wasteful movement caused by the manipulator moving unintentionally at high speed can be avoided, thus enabling improved treatment efficiency. Furthermore, a highly-skilled operator can operate the manipulator in a wide operating range so as to achieve improved ease of treatment with fewer limitations and improved treatment efficiency. On the other hand, if the skill of the operator is low, improved treatment efficiency can be achieved by avoiding contact with surrounding tissue, which may be caused when the manipulator moves to an unintended range.

In the above aspect, the history information may be the number of times the manipulator is used by the operator, and the one or more processors may configured to estimate that the skill of the operator which becomes higher as the number of times the manipulator has been used increases.

Accordingly, the skill of the operator can be estimated more readily in accordance with the number of times the manipulator has been used.

In the above aspect, the history information may be a cumulative usage time for which the manipulator is cumulatively used by the operator, and the controller may estimate that the skill of the operator becomes higher as the cumulative usage time increases.

Accordingly, the skill of the operator can be estimated more readily in accordance with the cumulative usage time.

In the above aspect, the history information may be a non-usage period in which the manipulator is not used by the operator, and the one or more processors may configured to estimate that the skill of the operator which becomes lower as the non-usage period increases.

Accordingly, it can be readily estimated that the skill of an operator with a long lapse of a non-usage period has deteriorated.

In the above aspect, the history information may be a time required for a single treatment process and may be stored for each type of treatment, and the one or more processors may configured to estimate that the skill of the operator which becomes higher as the required time decreases.

Accordingly, the skill of the operator can be readily estimated in accordance with how short the required time is for each of the multiple types of treatment with different standard required times.

Another aspect of the present invention provides a medical manipulator system including: a manipulator including an end effector configured to treat a patient and a driver configured to drive the end effector; an operation input unit configured to generate an operation command for the manipulator; and a first storage configured to store a history information of each operator; a second storage configured to store medical information; a display configured to display a state of the manipulator; and a controller comprising one or more processors, the one or more processors configured to: receive identification information of an operator by inputting of the operation input unit; get the history information of the operator from the first storage based on the identification information; estimate a skill of the operator based on the history information; get the medical information from the second storage based on the estimated skill; and control the display so as to display the medical information.

According to this aspect, when the operator inputs the identification information via the identification-information input unit and operates the operation input unit, the controller controls the driver based on the operation command input via the operation input unit so as to actuate the surgical section of the manipulator, whereby medical treatment is performed on the patient. Then, the history information of the operation performed on the operation input unit by the operator during this treatment is stored in the history-information storage unit. When the operator performs subsequent treatment, the history information stored in the history-information storage unit in association with the identification information is read, and the medical information according to the skill of the operator estimated based on the history information is displayed on the display unit.

For a highly-skilled operator, information for further improving the treatment efficiency is displayed. If the skill of the operator is low, medical information for improving the accuracy of the treatment is displayed, thus enabling improved treatment efficiency.

In the above aspect, the medical information may be medical-device information.

Accordingly, a medical device suitable for the skill can be used.

In the above aspect, the medical information may be learning-opportunity information.

Accordingly, an appropriate opportunity for skill improvement can be provided to the operator.

In the above aspect, the second storage may be connected to a network.

Accordingly, the medical information can be constantly and readily maintained in an up-to-date status.

The present invention is advantageous in that it enables improved efficiency of medical treatment regardless of the skill of an operator.

REFERENCE SIGNS LIST 1, 13 medical manipulator system
2 operation input unit
3 manipulator
4 controller
5 identification-information input unit
6 history-information storage unit
7 driver
10 surgical instrument (surgical section)
14 display unit
15 medical-information storage unit
O operator
P patient

The invention claimed is:

1. A medical manipulator system comprising:
a manipulator including an end effector configured to treat a patient and a driver configured to drive the end effector;
an operation input unit configured to generate an operation command for the manipulator;
a storage configured to store a history information of each operator; and
a controller comprising one or more processors, the one or more processors configured to:
receive identification information of an operator by inputting of the operation input unit;
get the history information of the operator from the storage based on the identification information;
estimate a skill of the operator based on the history information;
set a maximum operating speed of the manipulator and/or an operating range of the manipulator in proportion to the skill;
qualify the operation command based on the maximum operating speed and/or the operating range; and
control the driver based on the qualified operation command.

2. The medical manipulator system according to claim 1, wherein the history information is the number of times the manipulator is used by the operator, and
wherein the one or more processors configured to estimate the skill of the operator which becomes higher as the number of times the manipulator has been used increases.

3. The medical manipulator system according to claim 1, wherein the history information is a cumulative usage time for which the manipulator is cumulatively used by the operator, and
wherein the one or more processors configured to estimate the skill of the operator which becomes higher as the cumulative usage time increases.

4. The medical manipulator system according to claim 1, wherein the history information is a non-usage period in which the manipulator is not used by the operator, and
wherein the one or more processors configured to estimate the skill of the operator which becomes lower as the non-usage period increases.

5. The medical manipulator system according to claim 1, wherein the history information is a time required for a single treatment process and is stored for each type of treatment, and
wherein the one or more processors configured to estimate the skill of the operator which becomes higher as the required time decreases.

6. A medical manipulator system comprising:
a manipulator including an end effector configured to treat a patient and a driver configured to drive the end effector;
an operation input unit configured to generate an operation command for the manipulator; and a first storage configured to store a history information of each operator;
a second storage configured to store medical information;
a display configured to display a state of the manipulator; and
a controller comprising one or more processors, the one or more processors configured to:
  receive identification information of an operator by inputting of the operation input unit;
  get the history information of the operator from the first storage based on the identification information;
  estimate a skill of the operator based on the history information;
  get the medical information from the second storage based on the estimated skill; and
  control the display so as to display the medical information.

7. The medical manipulator system according to claim 6, wherein the medical information is medical-device information.

8. The medical manipulator system according to claim 6, wherein the medical information is learning-opportunity information.

9. The medical manipulator system according to claim 6, wherein the second storage is connected to a network.

* * * * *